United States Patent
Ni et al.

(10) Patent No.: US 12,276,809 B2
(45) Date of Patent: Apr. 15, 2025

(54) SUPER-RESOLUTION IMAGING SYSTEM AND METHOD, AND NUCLEIC ACID SEQUENCING IMAGING SYSTEM AND METHOD

(71) Applicant: BGI SHENZHEN, Shenzhen (CN)

(72) Inventors: Jielei Ni, Shenzhen (CN); Ming Ni, Shenzhen (CN); Fan Zhou, Shenzhen (CN); Zeyu Su, Shenzhen (CN); Ke Ji, Shenzhen (CN); Dong Wei, Shenzhen (CN); Mengzhe Shen, Shenzhen (CN); Yuanqing Liang, Shenzhen (CN); Mei Li, Shenzhen (CN); Xun Xu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 95 days.

(21) Appl. No.: 17/769,428

(22) PCT Filed: Mar. 9, 2020

(86) PCT No.: PCT/CN2020/078444
§ 371 (c)(1),
(2) Date: Apr. 15, 2022

(87) PCT Pub. No.: WO2021/179127
PCT Pub. Date: Sep. 16, 2021

(65) Prior Publication Data
US 2024/0085717 A1 Mar. 14, 2024

(51) Int. Cl.
*G01N 21/00* (2006.01)
*C12Q 1/6869* (2018.01)
(Continued)

(52) U.S. Cl.
CPC .......... *G02B 27/58* (2013.01); *C12Q 1/6869* (2013.01); *G01N 21/6428* (2013.01);
(Continued)

(58) Field of Classification Search
CPC .................................................. G01N 21/6486
See application file for complete search history.

(56) References Cited

U.S. PATENT DOCUMENTS

2017/0322406 A1* 11/2017 Sirat ................... G01N 21/6458
2017/0329122 A1 11/2017 Osawa
2018/0164571 A1 6/2018 Ouchi

FOREIGN PATENT DOCUMENTS

CN 107389631 A 11/2017

* cited by examiner

Primary Examiner — Dani Fox
(74) Attorney, Agent, or Firm — ScienBiziP, P.C.

(57) ABSTRACT

Disclosed are a super-resolution imaging system (1, 41, 51), a super-resolution imaging method, a biological sample identification system (4, 61) and method, a nucleic acid sequencing imaging system (5) and method, and a nucleic acid identification system (6) and method. The super-resolution imaging system (1, 41, 51) includes an illumination system (A) and an imaging system (B). The illumination system (A) outputs excitation light to irradiate a biological sample to generate excited light, and the imaging system (B) collects and records the excited light to generate an excited light image. The illumination system (A) includes an excitation light source (10, 10a) and a structured light generation and modulation device (11, 11a). The excitation light source (10, 10a) outputs the excitation light, and the structured light generation and modulation device (11, 11a) modulates the excitation light into structured light to irradiate the biological sample to generate the excited light.

19 Claims, 11 Drawing Sheets

(51) Int. Cl.
*G01N 21/64* (2006.01)
*G02B 21/14* (2006.01)
*G02B 21/16* (2006.01)
*G02B 21/36* (2006.01)
*G02B 27/28* (2006.01)
*G02B 27/58* (2006.01)

(52) U.S. Cl.
CPC ......... *G01N 21/6458* (2013.01); *G02B 21/14* (2013.01); *G02B 21/16* (2013.01); *G02B 21/36* (2013.01); *G02B 27/286* (2013.01); *G01N 2021/6439* (2013.01)

SUPER-RESOLUTION IMAGING SYSTEM AND METHOD, AND NUCLEIC ACID SEQUENCING IMAGING SYSTEM AND METHOD

TECHNICAL FIELD

The present disclosure relates to the field of imaging, in particular to a super-resolution imaging system and method, and a nucleic acid sequencing imaging system and method.

BACKGROUND ART

Existing high-throughput sequencing instruments mainly use ordinary wide-field fluorescence microscopy imaging technology to achieve signal collection. Fluorescent light from bases on the surface of a sequencing chip is first collected by an objective lens, and then the fluorescent light of different wavelengths is separated by one or several groups of dichroic mirrors, then converged by a tube lens respectively, and finally imaged on a CCD/CMOS surface. Subject to the diffraction limit, the resolution of the ordinary wide-field fluorescence microscopy technology can only reach about $0.61\lambda/NA$, which restricts the density of DNA samples on the sequencing chip and therefore restricts the sequencing throughput of a sequencer. Generally, the high-throughput sequencing instruments using the ordinary wide-field fluorescence microscopy imaging technology have the following problems:
1) Subject to the optical diffraction limit, the sequencing throughput is low.
2) The spacing of the DNA samples on the sequencing chip needs to be larger than the optical resolution, so the sample density is limited and the chip utilization is low.
3) The limited density of the DNA samples on the sequencing chip leads to low reagent utilization and high reagent cost.

In addition, existing super-resolution imaging technology usually have problems such as slow imaging, which restrict its application in high-throughput sequencing technology.

SUMMARY OF INVENTION

In view of this, there is a need to provide a super-resolution imaging system and method, a biological sample identification system and method, a nucleic acid sequencing imaging system and method, and a nucleic acid identification system and method to solve at least one of the problems in the prior art.

In a first aspect, the present disclosure provide a super-resolution imaging system, comprising an illumination system and an imaging system, the illumination system being configured to output excitation light to irradiate a biological sample to generate excited light, and the imaging system being configured to collect and record the excited light to generate an excited light image, wherein the illumination system comprises an excitation light source and a structured light generation and modulation device, the excitation light source is configured to output the excitation light, the structured light generation and modulation device is configured to modulate the excitation light into structured light to irradiate the biological sample to generate the excited light, the structured light generation and modulation device comprises a structured light control device, the structured light control device being configured to control the structured light generation and modulation device to change a phase of the structured light output by the structured light generation and modulation device and a direction of an illumination pattern of the structured light projected on the biological sample, and the imaging system is configured to photograph images of excited light excited by excitation light of at least one wavelength in at least one imaging field of view, in conjunction with a change in the phase of the structured light and/or the direction of the illumination pattern.

In at least one embodiment, the structured light generation and modulation device further comprises a polarization control system and a diffraction splitting device, the polarization control system is configured to adjust a polarization direction of the excitation light, the diffraction splitting device is configured to split the excitation light into multiple beams to form the structured light with a specific phase and a specific illumination pattern direction, and the structured light control device is configured to control the diffraction splitting device to change the phase of the structured light and the direction of the illumination pattern, and to control the polarization control system so that the illumination pattern of the structured light in any phase and any direction meets a preset requirement.

In at least one embodiment, the structured light control device is configured to control the polarization control system so that a contrast of the illumination pattern of the structured light meets the preset requirement.

In at least one embodiment, the structured light control device is configured to control the diffraction splitting device to move linearly to change the phase of the structured light, and to control the diffraction splitting device to rotate to change the direction of the illumination pattern of the structured light.

In at least one embodiment, the super-resolution imaging system further comprises an objective lens, and the structured light generation and modulation device further comprises a focusing device, the focusing device is configured to focus the structured light ejected from the diffraction splitting device to the objective lens, and the objective lens is configured to eject the structured light as parallel light to the biological sample and form interference fringes at a certain angle on a plane of the biological sample.

In at least one embodiment, the diffraction splitting device comprises a phase grating, and the polarization control system comprises a polarizer.

In at least one embodiment, the phase grating and the polarizer together are arranged on a one-dimensional moving platform, and the one-dimensional moving platform is arranged on a turntable, and the structured light control device is configured to control the one-dimensional moving platform to bring the phase grating and the polarizer to into movement to change the phase of the structured light, and to control the turntable to bring the phase grating and the polarizer into rotation to change the direction of the illumination pattern of the structured light.

In at least one embodiment, the focusing device comprises a first lens, a second lens and a third lens, with a stopper arranged between the first lens and the second lens, the stopper is configured to shield and block part of the structured light from entering a subsequent optical path.

In at least one embodiment, the polarizer is configured to convert the excitation light into linearly polarized light, and the phase grating is configured to convert the linearly polarized light into +1st-order, −1st-order, and 0th-order diffracted light, the 0th-order diffracted light is blocked by the stopper, and the +1st-order diffracted light and the −1st-order diffracted light are focused to a back focal plane of the objective lens after passing through the second lens and the third lens.

In at least one embodiment, the structured light generation and modulation device further comprises an adaptive optics device configured to shape a wavefront of the structured light.

In at least one embodiment, the structured light control device is further configured to control the adaptive optical device to optimize a contrast and/or a uniformity of the structured light.

In at least one embodiment, the super-resolution imaging system further comprising a master control device configured to control the excitation light source, the structured light generation and modulation device, and the imaging system to work coordinately.

In a second aspect, the present disclosure provide a super-resolution imaging method, comprising:
controlling an excitation light source of an illumination system in a super-resolution imaging system to be started, so that the illumination system outputs and irradiates structured light to a biological sample and the biological sample generates excited light;
controlling the structured light output from the illumination system to be in a first phase and an illumination pattern of the structured light to be in a first direction, and photographing a first image of the excited light;
controlling the structured light output from the illumination system to be in a second phase different from the first phase and the illumination pattern of the structured light to be in the first direction, and photographing a second image of the excited light;
controlling the structured light output from the illumination system to be in the second phase and the illumination pattern of the structured light to be in a second direction different from the first direction, and photographing a third image of the excited light; and/or
controlling the structured light output from the illumination system to be in the second phase and the illumination pattern of the structured light to be in a third direction different from the first direction and the second direction, or controlling the structured light output from the illumination system to be in the first phase and the illumination pattern of the structured light to be in the second direction, and photographing a fourth image of the excited light.

In at least one embodiment, the structured light is controlled to be in different phases by linearly moving a diffraction splitting device of the illumination system, and the illumination pattern of the structured light is controlled to be in different directions by rotating the diffraction splitting device, and the illumination pattern of the structured light in each direction and each phase meets a preset requirement by controlling a polarization control system to move or rotate.

In at least one embodiment, the illumination pattern of the structured light meeting a preset requirement comprises a contrast of the illumination pattern of the structured light meeting a preset requirement.

In at least one embodiment, the super-resolution imaging method further comprises: switching a wavelength of the excitation light and repeating steps of switching the phase and/or the direction of the structured light and photographing images of the excited light.

In at least one embodiment, after steps of switching the phase and/or the direction of the structured light and photographing an image of the excited light, the super-resolution imaging method further comprises: switching the wavelength of the excitation light and repeating the switching and photographing step.

In at least one embodiment, the super-resolution imaging method further comprises: switching an imaging field of view of the super-resolution imaging system and repeating steps of switching the phase and/or the direction of the structured light and photographing images of the excited light.

In at least one embodiment, after steps of switching the phase and/or the direction of the structured light and photographing an image of the excited light, the super-resolution imaging method further comprises: switching an imaging field of view of the super-resolution imaging system and repeating the switching and photographing step.

A third aspect of the present disclosure provide a biological sample identification system, comprising:
any one of the super-resolution imaging systems above; and
an image reconstruction and biological feature identification device configured to receive exited light images output from the super-resolution imaging system, and perform image reconstruction based on images of excited light excited by excitation light of the same wavelength in the same imaging field of view to obtain a reconstructed super-resolution image, and identity a biological feature of the biological sample corresponding to the excited light in the imaging field of view according to the reconstructed super-resolution image.

A fourth aspect of the present disclosure provide a biological sample identification method, comprising:
acquiring images of excited light excited by excitation light of the same wavelength in at least an imaging field of view by using any one of the super-resolution imaging methods above;
performing image reconstruction based on the images of the excited light excited by the excitation light of the same wavelength in the same imaging field of view to obtain a reconstructed super-resolution image; and
identifying a biological feature of a biological sample corresponding to the excited light in the imaging field of view according to the reconstructed super-resolution image.

A fifth aspect of the present disclosure provide a nucleic acid sequencing imaging system comprising any one of the super-resolution imaging systems above, the super-resolution imaging system being configured to irradiate a nucleic acid sample and photograph images of exited light ejected from the nucleic acid sample.

A sixth aspect of the present disclosure provide a nucleic acid sequencing imaging method, wherein the nucleic acid sequencing imaging method uses any one of the super-resolution imaging methods above to excite a nucleic acid sample to eject excited light and to photograph images of the excited light.

A seventh aspect of the present disclosure provide a nucleic acid identification system, comprising the biological sample identification system above, the biological sample identification system being configured to identify the class of a base of a nucleic acid sample.

A eighth aspect of the present disclosure provide a nucleic acid identification method, wherein the nucleic acid identification method uses the biological sample identification method above to identify the class of a base of a nucleic acid sample.

Using the super-resolution imaging system and method, the biological sample identification system and method, the nucleic acid sequencing imaging system and method, and the nucleic acid identification system and method provided in the embodiments of the present disclosure, a plurality of (e.g., 4) images of excited light are obtained by changing a direction and a phase of an output illumination pattern of structured light, and image reconstruction is performed by using the plurality of images to obtain a super-resolution image, and the layout and class of the biological sample can be identified by using the super-resolution image; in application to nucleic acid sequencing, the base layout and class can be identified. As few excited light images need to be photographed, the speed of biological sample identification is improved; and in application to nucleic acid sequencing, the speed of base identification can be improved. Using the super-resolution imaging technology can improve the density of samples on the sample carrier, thereby solving the problems of low imaging efficiency, limited sample layout density, and low utilization of the sample carrier due to the use of ordinary wide-field fluorescence microscopy imaging technology in the prior art; and in application to nucleic acid sequencing, it can solve the problems of a low sequencing throughput, limited chip density, low chip utilization, and low utilization of reagents.

BRIEF DESCRIPTION OF DRAWINGS

To describe technical solutions in the embodiments of the present disclosure more clearly, drawings to be used in the embodiments of the present disclosure will be introduced briefly below. Obviously, the drawings described below only represent some embodiments of the present disclosure, and those of ordinary skill in the art can also obtain other drawings according to these drawings without creative work.

The present disclosure will be further described by using the following specific embodiments in conjunction with the above-mentioned drawings.

DESCRIPTION OF SYMBOLS OF MAIN COMPONENTS

| | | | |
|---|---|---|---|
| Super-resolution imaging system | 1, 41, 51 | Illumination system | A |
| Imaging system | B | Excitation light source | 10, 10a |
| Structured light generation and modulation device | 11, 11a | Optical path guidance device | 12 |
| Objective lens | 13, 13a | Signal acquisition device | 14, 14a |
| Sample platform | 3 | Master control device | 15 |
| Sample carrier | 2, 2a | Polarization control system | 111 |
| Diffraction splitting device | 112 | Structured light generation and modulation device | 113, 113a |
| Focusing device | 114, 114a | Adaptive optics device | 115 |
| Dichroic Mirror | 121, 143, 12a | Camera | 141, 141a |
| Tube lens | 142, 142a | Autofocus module | 16 |
| Biological sample identification system | 4, 61 | Image reconstruction and biological feature identification device | 42 |
| Polarizer | 111a | Phase grating | 112a |
| Collimating lens | 115a | One-dimensional moving platform | 116 |
| Turntable | 117 | First lens | 1141a |
| Second lens | 1142a | Third lens | 1143a |
| Stopper | 118 | Step | S30-S34, S40-S46 |
| Nucleic acid sequencing imaging system | 5 | Nucleic acid identification system | 6 |

DETAIL DESCRIPTION

The technical solutions in the embodiments of the present disclosure will be described below clearly and completely in conjunction with the accompanying drawings in the embodiments of the present disclosure. Obviously, the described embodiments are only a part of the embodiments of the present disclosure, and not all the embodiments. All other embodiments obtained by those of ordinary skill in the art without creative work, based on the embodiments in the present disclosure, fall into the protection scope of the present disclosure.

It is to be noted that when a component is considered to be "arranged on" another component, it may be arranged directly on another component or there may also be an intermediate component. The term "and/or" as used herein encompasses all and any combinations of one or more associated listed items.

Figure 1:
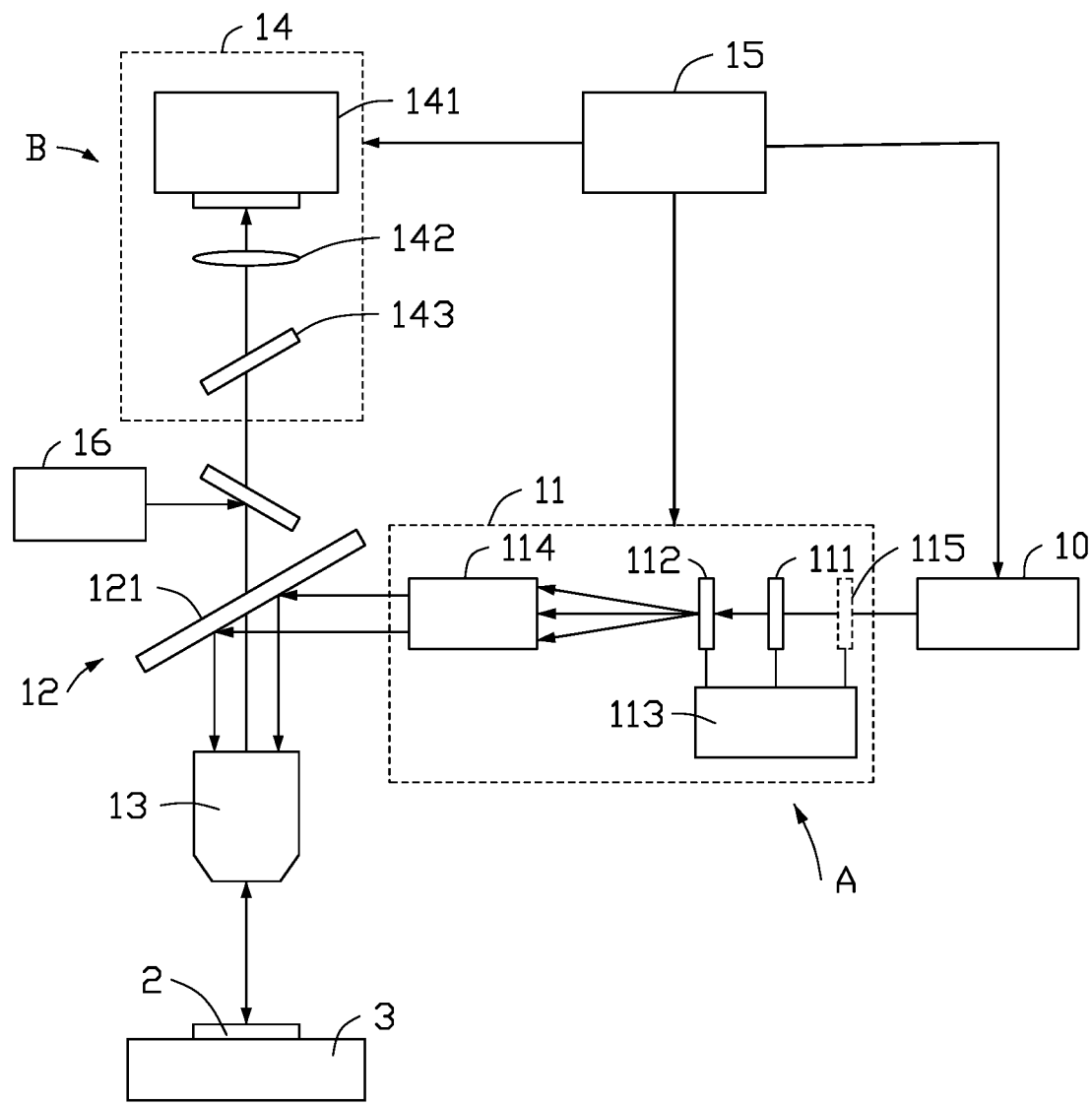
FIG. 1 is a structural diagram of a super-resolution imaging system provided in an embodiment of the present disclosure.

Referring to FIG. 1, which shows a wide-field super-resolution imaging system in an embodiment of the present disclosure. The super-resolution imaging system 1 includes an excitation light source 10, a structured light generation and modulation device 11, an optical path guidance device 12, an objective lens 13 and a signal acquisition device 14. The excitation light source 10, the structured light generation and modulation device 11, the optical path guidance device 12 and the objective lens 13 constitute an illumination system A of the super-resolution imaging system 1, and the objective lens 13, the optical path guidance device 12 and the signal acquisition device 14 constitute an imaging system B of the super-resolution imaging system 1.

The excitation light source 10 outputs excitation light; after passing through the structured light generation and modulation device 11, the excitation light is modulated into structured light with a specific illumination pattern direction and phase; and the structured light is guided by the optical path guidance device 12 to the objective lens 13, and is projected by the objective lens 13 onto a sample carrier 2 loaded with a treated biological sample. The biological sample may be a nucleic acid (DNA and RNA), proteins or cells, etc. In this embodiment, the sample carrier 2 is placed on a sample platform 3. The sample platform 3 is a movable platform configured to move the sample carrier 2 so that biological samples at different positions on the sample carrier 2 can be sequentially irradiated by the excitation light. In other embodiments, the sample platform 3 may not be used. In this embodiment, the excitation light excites a marker on the biological sample to generate the excited light (e.g., excited fluorescent light), and the excited light is collected by the objective lens 13 and then guided by the optical path guidance device 12 to the signal acquisition device 14, and the signal acquisition device 14 records the excited light and generates an excited light image. In this embodiment, the objective lens 13 collects the excited light on the one hand, and assists in generating the structured light projected onto the plane of the biological sample on the other hand. The objective lens 13 may be a low-power wide-field objective lens.

In this embodiment, the excitation light source 10 is a single-color or multi-color laser light source. Specifically, the excitation light source may be single-color, two-color or four-color laser for exciting a fluorescent marker on a biological feature (e.g., base) of the biological sample.

In this embodiment, the structured light generation and modulation device 11 includes a polarization control system 111, a diffraction splitting device 112, a structured light control device 113, and a focusing device 114. The polarization control system 111 is configured to adjust a polarization direction of the excitation light so that an illumination pattern of the structured light irradiated onto the biological sample meets a preset requirement, for example, so that the contrast of the illumination pattern of the structured light meets a requirement, or so that the illumination pattern of the structured light has the highest contrast. The polarization control system 111 may include optical elements such as a polarizer, a variable phase retarder, or a wave plate. The diffraction splitting device 112 is configured to split the excitation light into multiple beams, and in this embodiment, the diffraction splitting device 112 may include a beam splitter, a grating, a spatial light modulator, a digital micromirror device or optical fiber, etc. The structured light control device 113 is configured to control the polarization control system 111 and diffraction splitting device 112. By controlling the diffraction splitting device 112, the direction of the illumination pattern and the phase of the generated structured light are controlled, and at the same time, by controlling the polarization control system 111, the pattern of the structured light in each direction and each phase meets a preset requirement. Specifically, in an embodiment, the structured light control device 113 controls the polarization control system 111 and the diffraction splitting device 112 so that the polarization direction of the structured light changes with the direction of the structured light; and at the same time, the structured light control device 113 controls the polarization control system 111 according to a received external command or a preset parameter so that the illumination pattern of the structured light meets a preset requirement; for example, when receiving an external command indicating the illumination pattern of the structured light meets a preset contrast requirement, the structured light control device 113 controls the polarization control system 111 to maintains current settings, so that the illumination system continuously outputs the structured light the illumination pattern of which meets the preset contrast requirement until the polarization direction of the polarization control system 111 changes with the direction of the structured light. The external command indicating the illumination pattern of the structured light meets a preset contrast requirement may be a command manually entered by a user or a command output by an external device (not shown) after automatic judgment according to a preset condition.

The focusing device 114 is configured to focus the excitation light split into multiple beams by the diffraction splitting device 112 to the objective lens 13, and the objective lens 13 ejects the same as parallel light. In this embodiment, the focusing device 114 is a lens set, and the excitation light is focused by the lens set to a back focal plane of the objective lens 13 and ejected by the objective lens 13 as parallel light and forms interference fringes at a certain angle on the plane of the biological sample.

In this embodiment, the structured light generation and modulation device 11 may further include an adaptive optics device 115 configured to shape a wavefront of the structured light, and the structured light control device 113 may also be configured to control the adaptive optics device 115 to optimize the contrast and/or uniformity of the structured light or to keep the contrast and/or uniformity of the structured light optimal within an imaging field of view.

In this embodiment, the optical path guiding device 12 includes a dichroic mirror 121. The dichroic mirror 121 guides the structured light output from the structured light generation and modulation device 11 to the objective lens 13 on the one hand, and guides the excited light collected by the objective lens 13 to the signal acquisition device 14 on the other hand.

In this embodiment, the signal acquisition device 14 includes a plurality of cameras 141, a plurality of tube lenses 142, and one or more dichroic mirrors 143. The one or more dichroic mirrors 143 guide different excited light to different cameras 141. The plurality of cameras 141, the plurality of tube lenses 142, and the one or more dichroic mirrors 143 constitute a plurality of detection optical paths, of which only one detection optical path is shown in FIG. 1. The excited light guided to cameras 141 are converged by the corresponding tube lens 142 before entering the cameras 141, and is recorded by the cameras 141 to generate exited light images. In an embodiment, the signal acquisition device 14 may include four detection optical paths to acquire four types of excited light of the biological sample; in another embodiment, the signal acquisition device 14 may include two detection optical paths, and photographing is performed twice in each detection optical path to acquire two types of the excited light of the biological sample, and subsequently biological feature information of the biological sample is acquired and identified in conjunction with chemical and mathematical logic methods. Of course, in other embodiments, the signal acquisition device 14 may contain only one camera 141 and one tube lens 142 constituting one detection optical path, and subsequently biological feature information of the biological sample is acquired and identified in conjunction with chemical and mathematical logic methods.

In this embodiment, a master control device 15 is further included. The master control device 15 is configured to control the signal acquisition device 14, the excitation light source 10, the structured light generation and modulation device 11 and the sample platform to work coordinately. For example, under the control of the master control device 15, the signal acquisition device 14 photographs the excited light based on a frequency of switching the phase of the structured light and/or the direction of the illumination pattern by the structured light generation and modulation device 11, to obtain a plurality of different images of the same excited light. For example, under the control of the master control device 15, the excitation light source 10 outputs the excitation light of different wavelengths, and the structured light generation and modulation device 11 and the signal acquisition device 14 cooperatively switch the phase of the structured light and/or the direction of the illumination pattern and perform photographing, respectively, to obtain a plurality of different images of different excited light. For example, under the control of the master control device 15, the sample platform 3 moves the biological sample to switch the imaging field of view of the super-resolution imaging system 1 to obtain a plurality of different images of the excited light of the biological sample in different areas.

In this embodiment, the super-resolution imaging system 1 further includes an autofocus module 16. The autofocus module 16 is configured to emit detection light in real time to the sample carrier 2, receive detection light returned from the sample carrier 2, and detect in real time whether the sample carrier 2 is located on a focal plane of the objective lens 13 according to the returned detection light, and if the sample carrier 2 is not located on the focal plane of the objective lens 13, the autofocus module 16 sends a signal recording an out-of-focus direction and an out-of-focus distance of the sample carrier 2 to a device (not shown) that controls a relative distance between the sample carrier 2 and the objective lens 13, and this device causes the sample carrier 2 to return to the focal plane of the objective lens 13. In this embodiment, the detection light emitted by the autofocus module 16 is projected onto the sample carrier 2 through the optical path guidance device 12 and the objective lens 13, and the detection light returned from the sample carrier 2 returns to the autofocus module 16 through the objective lens 13 and the optical path guidance device 12 and is detected by the autofocus module 16.

In other embodiments, the autofocus module 16 may be omitted.

Figure 2:
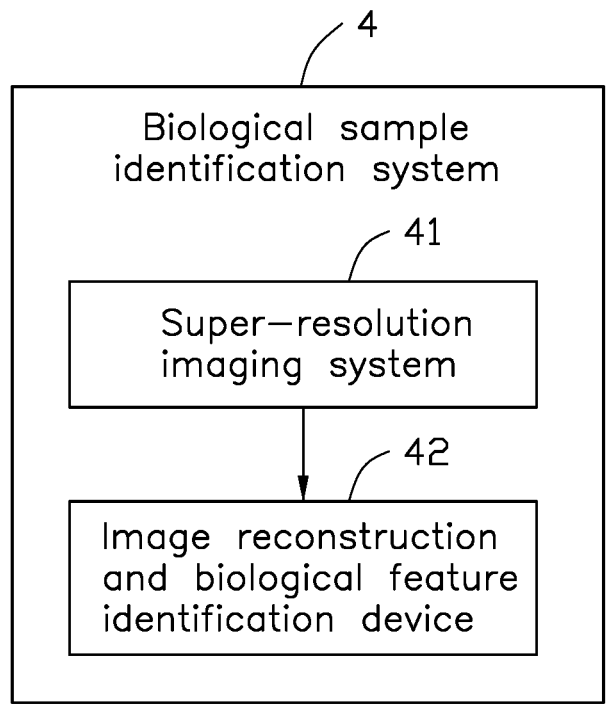
FIG. 2 is a structural diagram of a biological sample identification system provided in an embodiment of the present disclosure.

Referring to FIG. 2, which shows a schematic diagram of a biological sample identification system in an embodiment of the present disclosure. The biological sample identification system 4 includes a super-resolution imaging system 41 and an image reconstruction and biological feature identification device 42. The super-resolution imaging system 41 may be a super-resolution imaging system as introduced previously. The super-resolution imaging system acquires a number of (e.g., four) different images of excited light excited by at least a type of excitation light in at least a field of view by controlling the phase of the structured light irradiated to the biological sample and the direction of the illumination pattern of the structured light. The image reconstruction and biological feature identification device 42 may be any computing device with an image reconstruction program and a biological feature identification program installed therein. The image reconstruction program receives exited light images output from the super-resolution imaging system 41, and performs image reconstruction using a specific algorithm based on a plurality of images of excited light excited by excitation light of the same wavelength in the same imaging field of view to obtain a reconstructed super-resolution image. The specific algorithm may be, for example, an open-source SIM (Structured Illumination Microscopy) reconstruction algorithm. The biological feature identification program is configured to identify a biological feature (such as a base) of a biological sample corresponding to the excited light in the corresponding field of view according to the reconstructed super-resolution image. Both image reconstruction and biological feature identification in this embodiment can be carried out by using the prior art, and thus are not described specifically in this embodiment.

Figure 3:
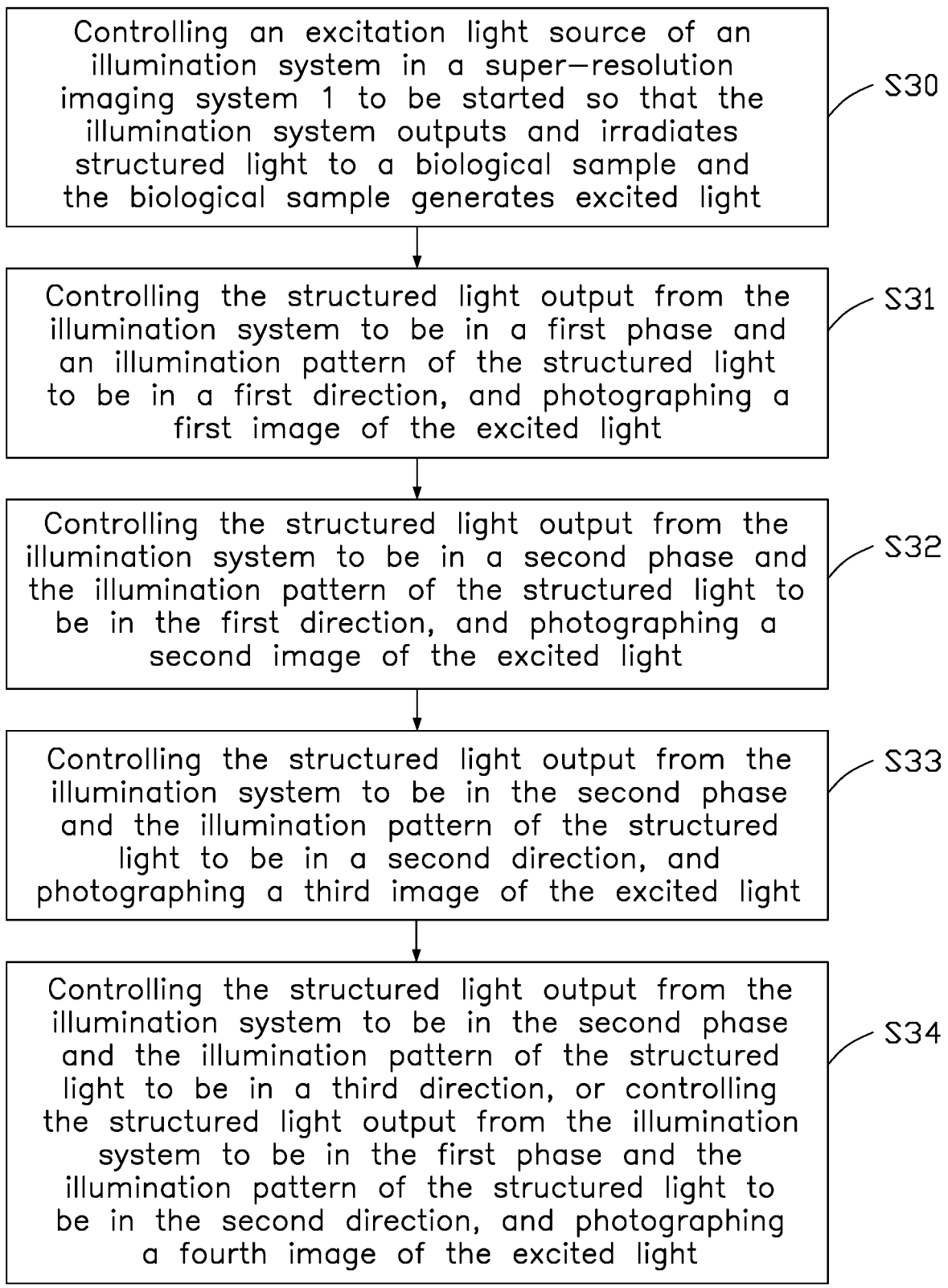
FIG. 3 is a flow diagram of a super-resolution imaging method provided in an embodiment of the present disclosure.

Referring to FIG. 3, which shows a flow diagram of a super-resolution imaging method provided in an embodiment of the present disclosure. The method may be implemented in conjunction with the super-resolution imaging system 1 shown in FIG. 1 or a similar super-resolution imaging system. Some steps in the method may be omitted and the order of some steps may be changed, as needed.

In this embodiment, description is made by using the super-resolution imaging implemented in conjunction with the super-resolution imaging system 1 shown in FIG. 1 as an example.

Step S30: controlling an excitation light source of an illumination system in a super-resolution imaging system 1 to be started so that the illumination system outputs and irradiates structured light to a biological sample and the biological sample generates excited light.

Step S31: controlling the structured light output from the illumination system to be in a first phase and an illumination pattern of the structured light to be in a first direction, and photographing a first image of the excited light.

In this embodiment, a diffraction splitting device 112 is controlled so that the structured light output from the lighting system A is in the first phase and the illumination pattern of the structured light is in the first direction, and at the same time, a polarization control system 111 is controlled by a structured light control device 113 so that the illumination pattern of the structured light in the first direction and first phase meets a preset requirement, for example, so that the contrast of illumination stripes of the illumination pattern meets a requirement.

Step S32: changing the phase of the structured light output from the illumination system to a second phase different from the first phase, controlling the structured light output from the illumination system to be in the second phase and the illumination pattern of the structured light to be in the first direction, and photographing a second image of the excited light.

Step S33: changing the direction of the illumination pattern of the structured light output from the illumination system to a second direction different from the first direction, controlling the structured light output from the illumination system to be in the second phase and the illumination pattern of the structured light to be in the second direction, and photographing a third image of the excited light.

Step S34: changing the direction of the illumination pattern of the structured light output from the illumination system to be in a third direction different from the first direction and the second direction and controlling the structured light output from the illumination system to be in the second phase and the illumination pattern of the structured light to be in the third direction, or changing the phase of the structured light output from the illumination system to the first phase and controlling the structured light output from the illumination system to be in the first phase and the illumination pattern of the structured light to be in the second direction, and photographing a fourth image of the excited light.

The steps of the present disclosure are not limited to the above order, but may also be adjusted as needed. In addition, the words "first", "second" and "third" used in the above expressions are only used to distinguish the relevant phases, directions or images, and do not indicate that the relevant phases, directions or images have a specific sequential order. In fact, the order of execution of the above steps S31-S34 is variable.

In this embodiment, the structured light control device 113 controls the phase of the structured light and the direction of the illumination pattern of the structured light by controlling the diffraction splitting device 112 to perform linear movement, rotation, etc.; and enables the illumination pattern of the structured light in each direction and each phase to meet a preset requirement by synchronously moving and rotating the diffraction splitting device 112 and the polarization control system 111.

In another embodiment, it may further include a step of photographing a fifth image, a sixth image, a seventh image, an eighth image and a ninth image of the excited light, and the phase of the structured light and/or the direction of the illumination pattern of the structured light are changed by controlling the diffraction splitting device 112 and the polarization control system 111, so that each photographed image of the excited light is different from the other images. For example, a correspondence relationship between the first to the ninth images and the phase of the structured light and the direction of the illumination pattern of the structured light may be shown in the following table:

| Image | Phase | Direction |
| --- | --- | --- |
| First image | First phase | First direction |
| Second image | Second phase | First direction |
| Third Image | Second phase | Second direction |
| Fourth image | Second phase | Third direction |
| Fifth Image | Third phase | Third direction |
| Sixth image | Third phase | Second direction |
| Seventh image | Third phase | First direction |
| Eighth image | First phase | Second direction |
| Ninth image | First phase | Third direction |

Similarly as described above, the above words "first" to "ninth" are only used to distinguish the images and do not indicate the images are in a specific sequential order. In fact, the numbering of the above images is not used to limit the order, and the order of image acquisition may be adjusted as needed in practical applications.

In other embodiments, the super-resolution imaging method may further include a step of: switching the wavelength of the excitation light and repeating steps S30-S34 to acquire multiple frames of images of the excited light excited by the excitation light of other wavelengths until the excited light excited by the excitation light of all predetermined wavelengths is photographed.

In other embodiments, after each step of switching the phase and/or direction of the structured light and photographing an image of the excited light in the super-resolution imaging method is completed, the method may further include: switching the wavelength of the excitation light and repeating the switching and photographing step until the excited light excited by the excitation light of all predetermined wavelengths is photographed.

In other embodiments, the super-resolution imaging method may further include a step of: moving a sample carrier 2 to switch an imaging field of view of the super-resolution imaging system 1 so that an objective lens 13 can collect the excited light emitted by biological samples at different positions of the sample carrier 2, and repeating steps S30-S34 to acquire multiple frames of images of the excited light at other positions until all positions predetermined to be imaged are photographed.

In other embodiments, after each step of switching the phase and/or direction of the structured light and photographing an image of the excited light in the super-resolution imaging method is completed, the method may further include: switching the imaging field of view of the super-resolution imaging system 1 and repeating the switching and photographing step to acquire images of the excited light at different positions until all positions predetermined to be imaged are photographed.

Figure 4:
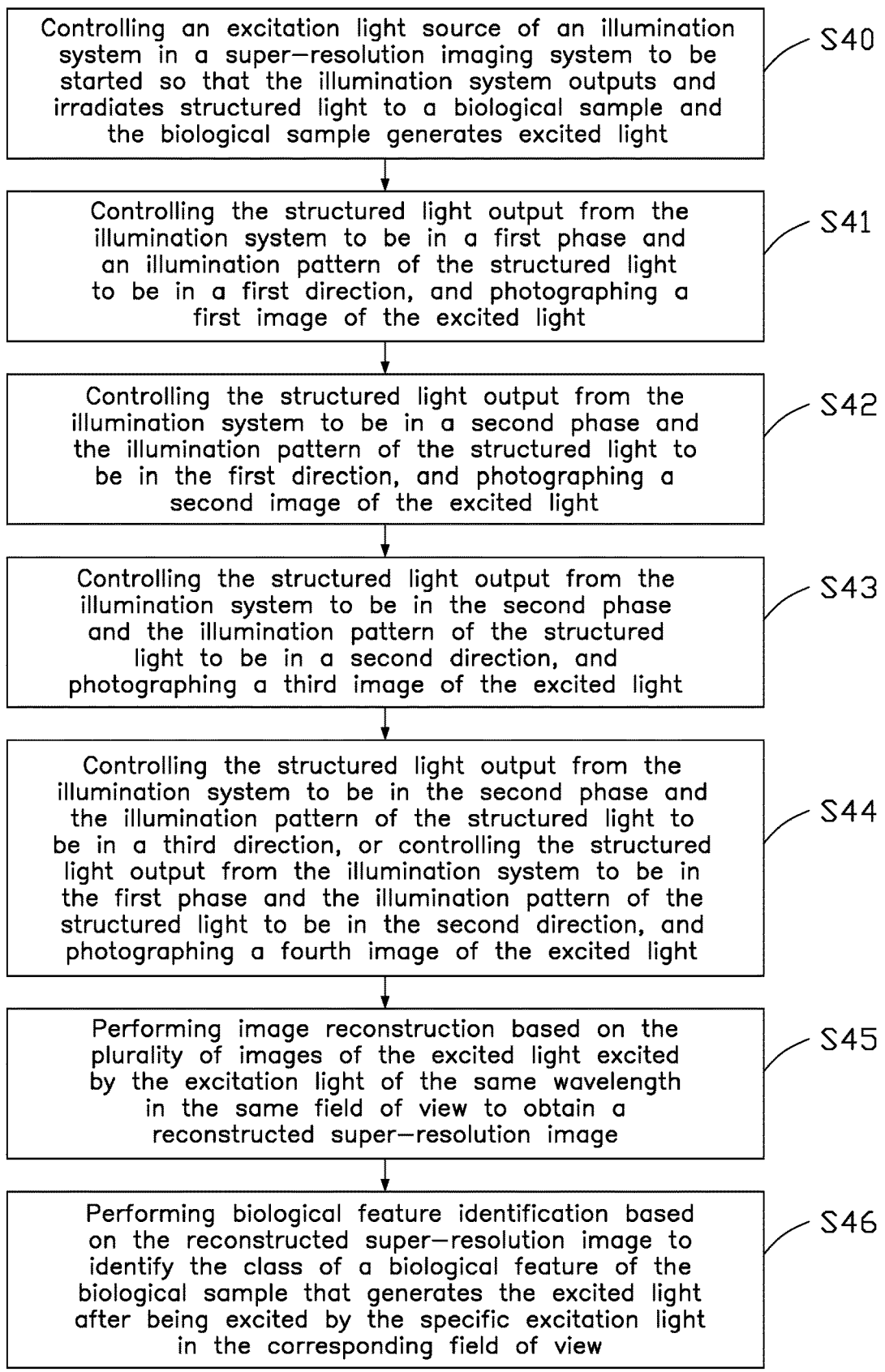
FIG. 4 is a flow diagram of a biological sample identification method provided in an embodiment of the present disclosure.

Referring to FIG. 4, which shows a flow diagram of a biological sample identification method provided in an embodiment of the present disclosure. The method may be implemented in conjunction with the biological sample identification system shown in FIG. 2 or a similar biological sample identification system. Some steps in the method may be omitted and the order of some steps may be changed, as needed.

Step S40: controlling an excitation light source of an illumination system in a super-resolution imaging system to be started so that the illumination system outputs and irradiates structured light to a biological sample and the biological sample generates excited light.

Step S41: controlling the structured light output from the illumination system to be in a first phase and an illumination pattern of the structured light to be in a first direction, and photographing a first image of the excited light.

Step S42: controlling the structured light output from the illumination system to be in a second phase different from the first phase and the illumination pattern of the structured light to be in the first direction, and photographing a second image of the excited light.

Step S43: controlling the structured light output from the illumination system to be in the second phase and the illumination pattern of the structured light to be in a second direction different from the first direction, and photographing a third image of the excited light.

Step S44: controlling the structured light output from the illumination system to be in the second phase and the illumination pattern of the structured light to be in a third direction different from the first direction and the second direction, or controlling the structured light output from the illumination system to be in the first phase and the illumination pattern of the structured light to be in the second direction, and photographing a fourth image of the excited light.

The above steps of the present application are not limited to the above order, and may also be adjusted as needed.

For details of the embodiment of the above steps, reference may be made to the previous description of the super-resolution imaging method in the present application, and it will not be repeated here. In addition, similarly, a fifth image, and even a sixth image, a seventh image . . . of the excited light may also be acquired by controlling the phase of the structured light irradiated to the biological sample and the direction of the illumination pattern of the structured light; similarly, a plurality of different images of the excited light excited by the excitation light of other wavelengths may also be acquired by changing the wavelength of the excitation light; and similarly, a plurality of different images of the excited light in other fields of view may also be acquired by changing the imaging field of view.

Step S45: performing image reconstruction based on the plurality of images of the excited light excited by the excitation light of the same wavelength in the same field of view to obtain a reconstructed super-resolution image.

In this embodiment, the reconstruction of the plurality of images of the excited light is performed by using SIM (Structured Illumination Microscopy) super-resolution reconstruction technology. The SIM super-resolution reconstruction technology may use many existing algorithms to perform reconstruction. For example, it may use an existing open-source SIM reconstruction algorithm to perform reconstruction.

Step S46: performing biological feature identification based on the reconstructed super-resolution image to identify a biological feature of the biological sample that generates the excited light after being excited by the specific excitation light in the corresponding field of view.

In this embodiment, the image-based identification of the biological feature of the biological sample (e.g., a base of a DNA sample) is performed by using the prior art and is not specifically introduced here.

Specific embodiments of the super-resolution imaging system and the super-resolution imaging method are given below to make further description in conduction with the super-resolution imaging system 1 and the super-resolution imaging method introduced previously in the present application.

Figure 5:
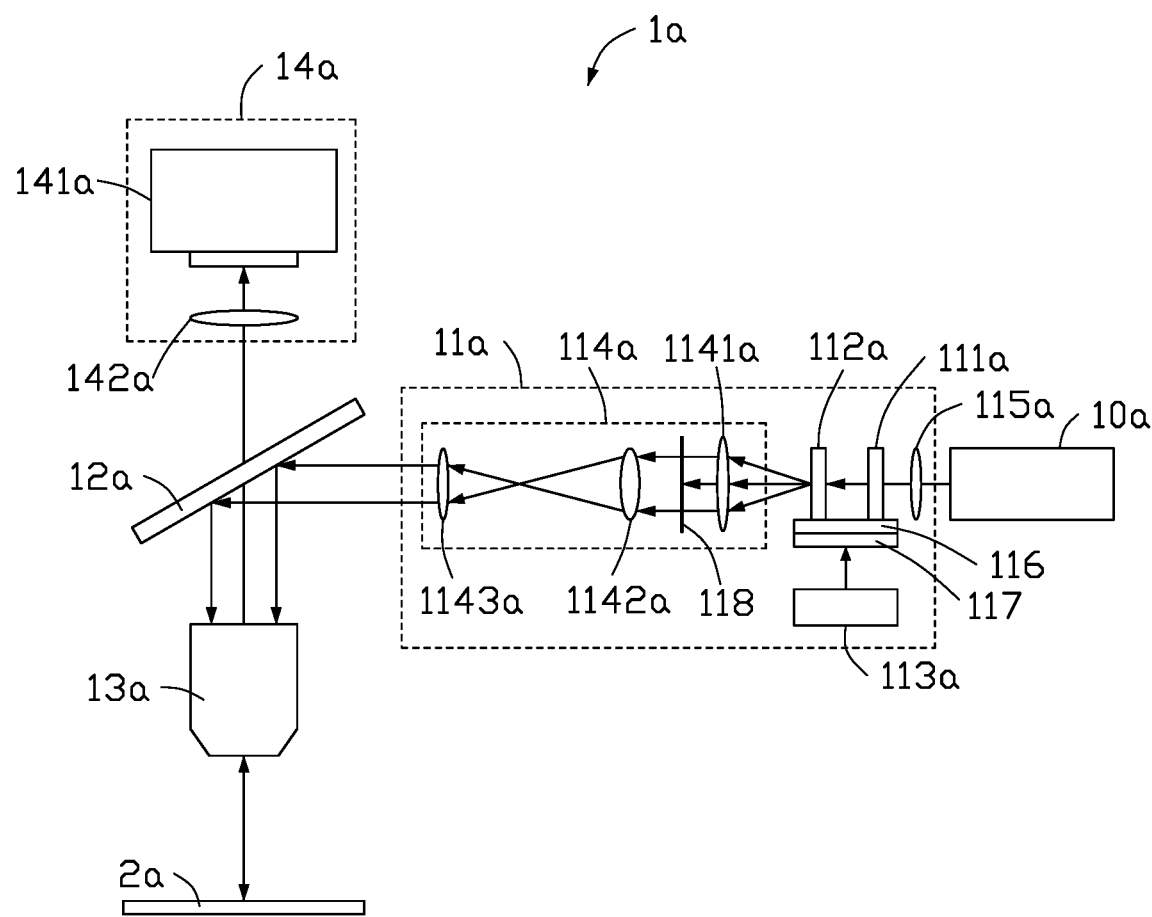
FIG. 5 is a schematic diagram of a specific embodiment of the super-resolution imaging system shown in FIG. 1 of the present disclosure.

Referring to FIG. 5, a super-resolution imaging system 1a includes an excitation light source 10a, a structured light generation and modulation device 11a, a dichroic mirror 12a, an objective lens 13a, and a signal acquisition device 14a, wherein the signal acquisition device 14a includes a camera 141a and a tube lens 142a. The structured light generation and modulation device 11a includes a polarizer 111a, a phase grating 112a, a structured light control device 113a, a focusing device 114a and a collimating lens 115a. The collimating lens 115a, the polarizer 111a, the phase grating 112a and the focusing device 114a are arranged behind the excitation light source 10a from near to far along an ejection direction of excitation light; the polarizer 111a and the phase grating 112a together are arranged on a one-dimensional moving platform 116; and the one-dimensional moving platform 116 is arranged, together with the polarizer 111a and the phase grating 112a, on a turntable 117. The structured light control device 113a is connected to the one-dimensional moving platform 116 and the turntable 117, for controlling the moving platform 116 to move and the turntable 117 to rotate to adjust the phase of output structured light and the direction of an illumination pattern of the structured light. The focusing device 114a includes a first lens 1141a, a second lens 1142a and a third lens 1143a, the first lens 1141a, the second lens 1142a and the third lens 1143a being arranged behind the phase grating 112a from near to far in the ejection direction of the excitation light. A stopper 118 is also provided between the first lens 1141a and the second lens 1142a, and the stopper 118 is configured to shield part of diffracted light and block it from entering the subsequent optical path. In this embodiment, the stopper 118 is provided on a back focus plane of the first lens 1141a.

Specifically, in this embodiment, the excitation light source 10a can emit excitation light of two wavelengths; the excitation light is collimated by the collimating lens 115a, and then enters the polarizer 111a and becomes linearly polarized light, a polarization direction of which is parallel to a scribed line direction of the phase grating 112a; and the linearly polarized light enters the phase grating 112a to generate +1st-order, −1st-order and 0th-order diffracted light. After the diffracted light is focused by the first lens 1141a, the 0th-order diffracted light is blocked by the stopper 118, and the +1st-order diffracted light and the −1st-order diffracted light are reflected and focused by the dichroic mirror 12a to a back focus plane of the objective lens 13a after passing through the second lens 1142a and the third lens 1143a, and then are ejected as parallel light at a certain angle to a sample carrier 2a. The +1st-order diffracted light and the −1st-order diffracted light overlap on the sample carrier 2a to produce interference fringes. The spacing of the interference stripes is d/2M, where d is scribed line spacing of the phase grating 112a, and M is a total magnification of the combination of the first lens 1141a, the second lens 1142a, the third lens 1143a and the objective lens 13a. Therefore, the excitation light of the two wavelengths produces interference fringes with the same spacing.

In this embodiment, the sample carrier 2a is located on an imaging plane of the objective lens 13a, which imaging plane is conjugate to a scribed line plane of the phase grating 112a and a sensor plane of the camera 141a. Two fluorescent markers are attached to the sample carrier 2a, and the excitation light of each wavelength can excite one of the fluorescent markers to produce excited light in a fluorescent form, and the excited light is collected by the objective lens 13a, passes through the dichroic mirror 12a and the tube lens 142a, and then is recorded by the camera 141a.

Three super-resolution imaging methods implemented by using the super-resolution imaging system 1a are introduced below.

Figure 6A:
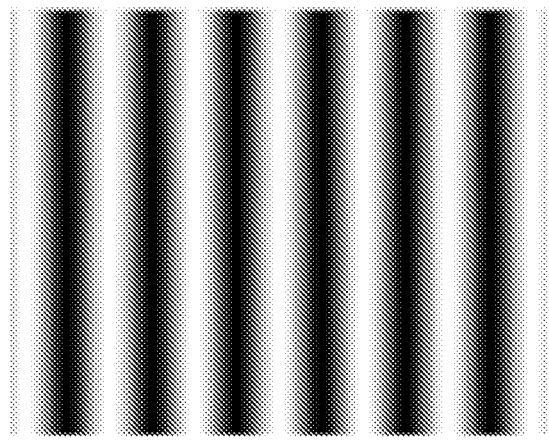
FIGS. 6A to 6I are schematic diagrams of interference fringes produced on a sample carrier using structured light output from the super-resolution imaging system shown in FIG. 5 in a super-resolution imaging method.

A first super-resolution imaging method is as follows:

In step I, the excitation light source 10a is started so that the excitation light source 10a first outputs excitation light of a first wavelength; after the excitation light of the first wavelength passes through the super-resolution imaging system 1a, structured light is output and irradiated to the sample carrier 2a to produce interference fringes as shown in FIG. 6A on the sample carrier 2a, and the structured light excites one of the fluorescent markers on the sample carrier 2a to generate first excited light, which is recorded by the camera 141a; next, the excitation light source 10a is switched to output excitation light of a second wavelength, and the excitation light of the second wavelength excites the other fluorescent marker on the sample carrier 2a to generate second excited light, which is recorded by the camera 141a.

Figure 6B:
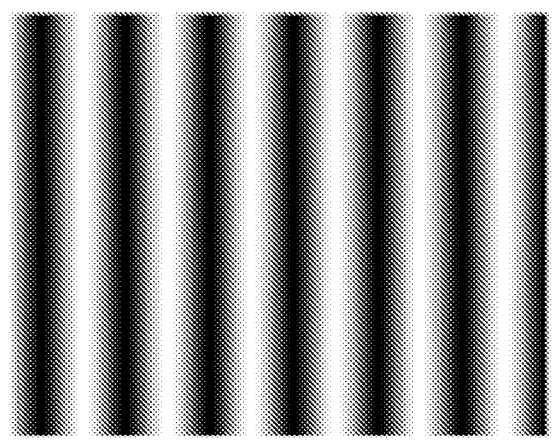

In step II, the structured light control device 113a controls the one-dimensional moving platform 116 to cause the phase grating 112a to move d/6 in a grating plane, where d is a grating period, so that the phase of the interference fringes on the sample carrier 2a shifts $2\pi/3$, as shown in FIG. 6B. The first excited light and the second excited light are then recorded in the same manner as in step I.

Figure 6C:
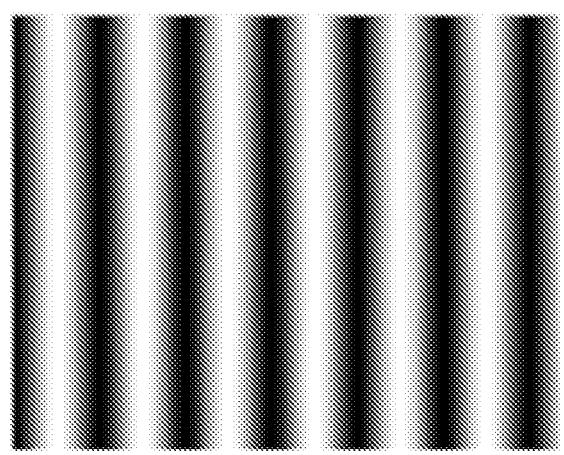

In step III, the structured light control device 113a continues controlling the one-dimensional moving platform 116 to cause the phase grating 112a to continue moving forward d/6 again in the grating plane, so that the phase of the interference fringes on the sample carrier 2a shifts $2\pi/3$ again, as shown in FIG. 6C. Then the first excited light and the second excited light are recorded in the same manner as in step I.

In step IV, the structured light control device 113a controls the one-dimensional moving platform 116 to cause the phase grating 112a to move backward d/3 and return to the position of the origin.

Figure 6D:
Figure 6E:
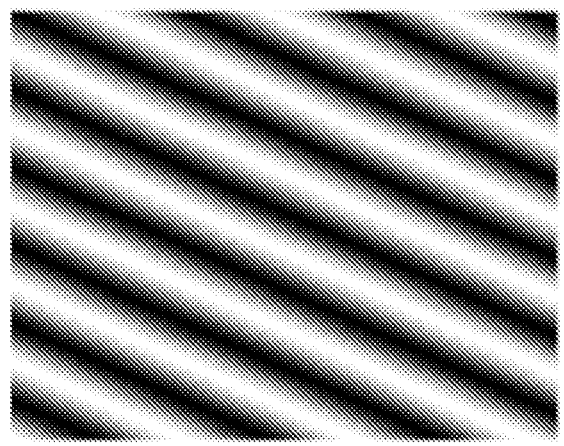
Figure 6F:
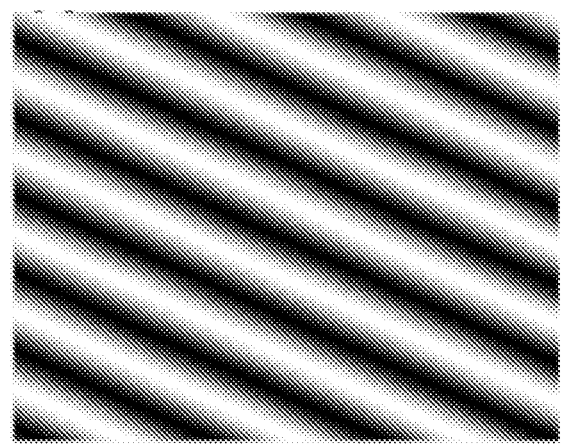

In step V, the structured light control 113a controls the turntable 117 to cause the phase grating 112a and the polarizer 111a to rotate 60 degrees along the grating plane. The first excited light and the second excited light generated when the interference fringes of the structured light are in different phases are then recorded successively in the same manner as in steps I to IV. The corresponding interference fringes are shown in FIGS. 6D-6F.

Figure 6G:
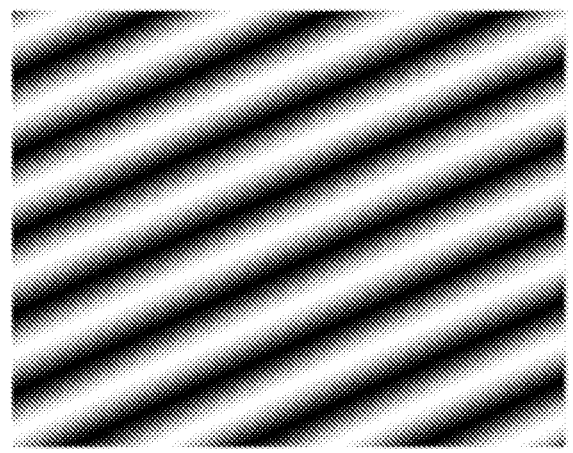
Figure 6H:
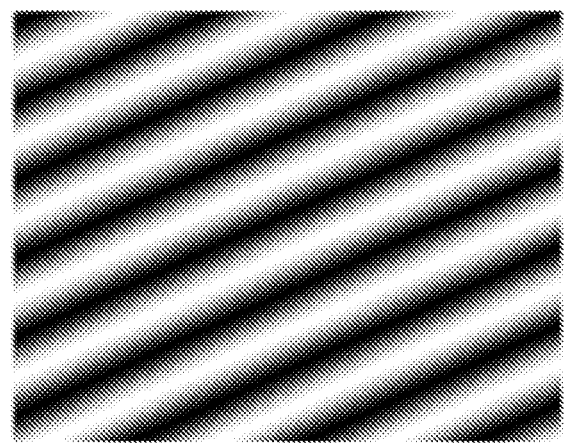
Figure 6I:
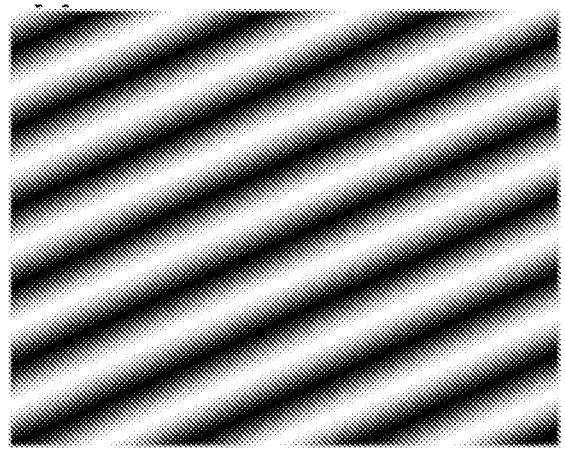

In step VI, the structured light control 113a controls the turntable 117 to cause the phase grating 112a and the polarizer 111a to continue rotating 60 degrees in the same direction along the grating plane. The first excited light and the second excited light generated when the interference fringes of the structured light are in different phases are then recorded successively in the same manner as in steps I to IV. The corresponding interference fringes are shown in FIGS. 6G-6I.

9 images of each type of excited light are obtained by the above steps. Super-resolution reconstruction is performed by using the 9 images of each type of excited light to obtain a super-resolution image of the excited light. Biological feature identification is performed on the super-resolution images of the two types of excited light to obtain biological features of all biological samples on the sample carrier 2a in the field of view.

Figure 7A:
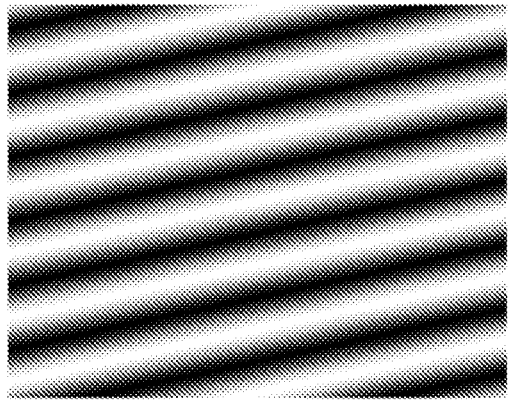
FIGS. 7A to 7D are schematic diagrams of interference fringes produced on a sample carrier using structured light output from the super-resolution imaging system shown in FIG. 5 in another super-resolution imaging method.

A second super-resolution imaging method is as follows:

In step I, the excitation light source 10a is started so that the excitation light source 10a first outputs excitation light of a first wavelength; after the excitation light of the first wavelength passes through the super-resolution imaging system 1a, structured light is output and irradiated to the sample carrier 2a to produce interference fringes as shown in FIG. 7A on the sample carrier 2a, and the structured light excites one of the fluorescent markers on the sample carrier 2a to generate first excited light, which is recorded by the camera 141a; next, the excitation light source 10a is switched to output excitation light of a second wavelength, and the excitation light of the second wavelength excites the other fluorescent marker on the sample carrier 2a to generate second excited light, which is recorded by the camera 141a.

Figure 7B:

In step II, the structured light control device 113a then controls the one-dimensional moving platform 116 to cause the phase grating 112a to move d/4 in a grating plane, where d is a grating period, so that the phase of the interference fringes on the sample carrier 2a shifts $\pi/2$, as shown in FIG. 7B. Then the first excited light and the second excited light are recorded in the same manner as in step I.

In step III, the structured light control device 113a controls the one-dimensional moving platform 116 to cause the phase grating 112a to move backward d/4 and return to the position of the origin.

Figure 7C:
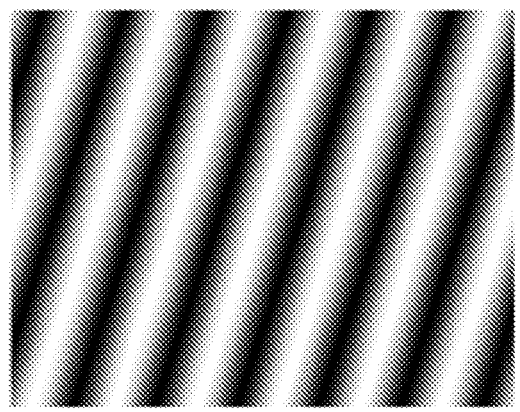

In step IV, the structured light control 113a controls the turntable 117 to cause the phase grating 112a and the polarizer 111a to rotate 60 degrees along the grating plane. The first excited light and the second excited light generated by the interference fringes of the structured light are then recorded in the same manner as in step I. The corresponding interference fringes are shown in FIG. 7C.

Figure 7D:

In step V, the structured light control 113a controls the turntable 117 to cause the phase grating 112a and the polarizer 111a to continue rotating 60 degrees in the same direction along the grating plane. The first excited light and the second excited light generated by the interference fringes of the structured light are then recorded in the same manner as in step I. The corresponding interference fringes are shown in FIG. 7D.

4 images of each type of excited light are obtained by the above steps. Super-resolution reconstruction is performed by using the 4 images of each type of excited light to obtain a super-resolution image of the excited light. Biological feature identification is performed on the super-resolution images of the two types of excited light to obtain biological features of all biological samples (e.g., bases of DNA samples) on the sample carrier 2a in the field of view.

Figure 8A:
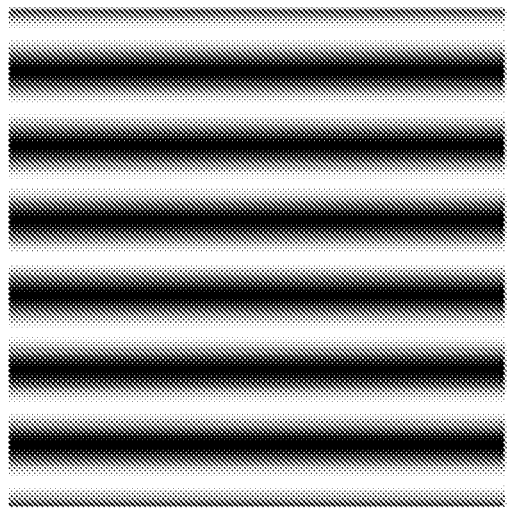
FIGS. 8A to 8D are schematic diagrams of interference fringes produced on a sample carrier using structured light output from the super-resolution imaging system shown in FIG. 5 in a third super-resolution imaging method of the present disclosure.

A third super-resolution imaging method is as follows:

In step I, the excitation light source 10a is started so that the excitation light source 10a first outputs excitation light of a first wavelength; after the excitation light of the first wavelength passes through the super-resolution imaging system 1a, structured light is output and irradiated to the sample carrier 2a to produce interference fringes as shown in FIG. 8A on the sample carrier 2a, and the structured light excites one of the fluorescent markers on the sample carrier 2a to generate first excited light, which is recorded by the camera 141a; next, the excitation light source 10a is switched to output excitation light of a second wavelength, and the excitation light of the second wavelength excites the other fluorescent marker on the sample carrier 2a to generate second excited light, which is recorded by the camera 141a.

Figure 8B:
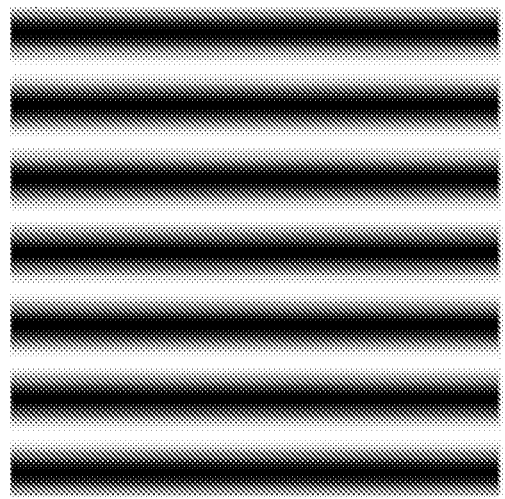

In step II, the structured light control device 113a then controls the one-dimensional moving platform 116 to cause the phase grating 112a to move d/4 in a grating plane, where d is a grating period, so that the phase of the interference fringes on the sample carrier 2a shifts $\pi/2$, as shown in FIG. 8B. Then the first excited light and the second excited light are recorded in the same manner as in step I.

In step III, the structured light control device 113a controls the one-dimensional moving platform 116 to cause the phase grating 112a to move backward d/4 and return to the original position.

Figure 8C:
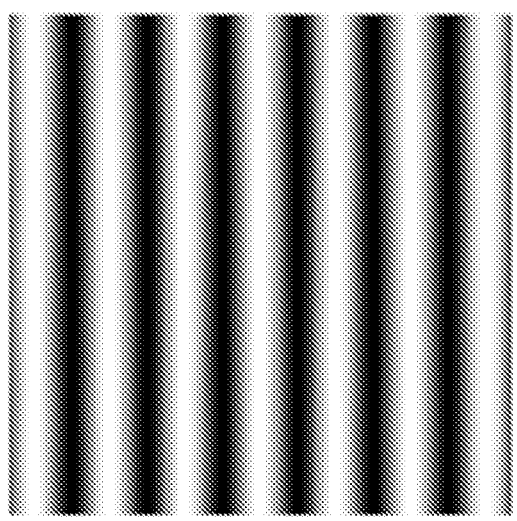

In step IV, the structured light control 113a controls the turntable 117 to cause the phase grating 112a and the polarizer 111a to rotate 90 degrees along the grating plane. The first excited light and the second excited light of the interference fringes of the structured light in different phases are then recorded successively in the same manner as in steps I to III. The corresponding interference fringes are shown in FIG. 8C.

Figure 8D:
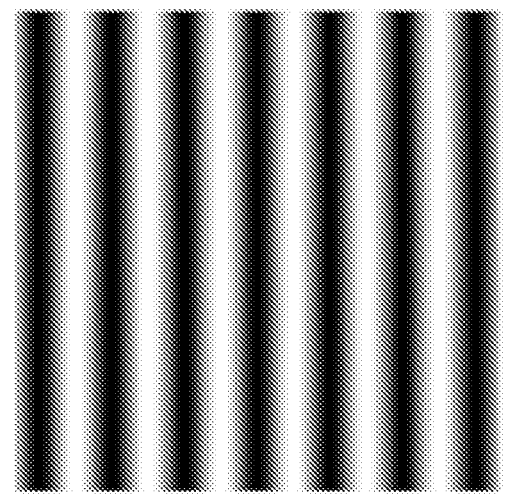

In step V, the structured light control device 113a controls the one-dimensional moving platform 116 to cause the phase grating 112a to move d/4 grating period, so that the phase of the interference fringes on the sample carrier 2a shifts $\pi/2$, as shown in FIG. 8D. Then the first excited light and the second excited light generated when the interference fringes of the structured light are in different phases are recorded in the same manner as in steps I to III.

In step VI, the structured light control device 113a controls the one-dimensional moving platform 116 to cause the phase grating 112a to move backward d/4 and return to the position of the origin. In other embodiments, this step may also be omitted.

4 images of each type of excited light are obtained by the above steps. Super-resolution reconstruction is performed by using the 4 images of each type of excited light to obtain a super-resolution image of the excited light. Biological feature identification is performed on the super-resolution images of the two types of excited light to obtain biological features of all biological samples on the sample carrier 2a in the field of view.

Figure 9:
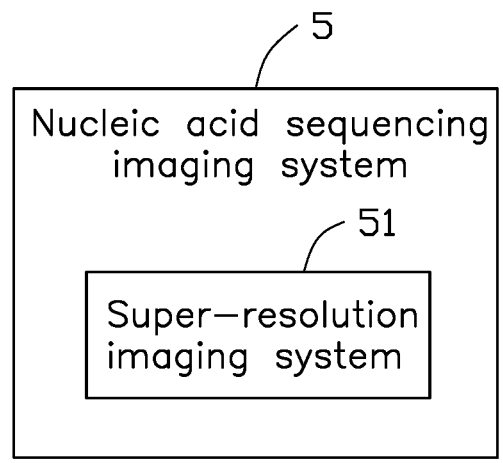
FIG. 9 is a schematic diagram of a nucleic acid sequencing imaging system provided in an embodiment of the present disclosure.

The super-resolution imaging system and method introduced in the above embodiments can be used in nucleic acid sequencing. Specifically, the present application further provides a nucleic acid sequencing imaging system and a nucleic acid sequencing imaging method. Referring to FIG. 9, the nucleic acid sequencing imaging system 5 includes a super-resolution imaging system 51. The super-resolution imaging system 51 may be any super-resolution imaging systems introduce in the above embodiments or a super-resolution imaging system obtained by improvement of any super-resolution imaging systems described above, and the super-resolution imaging system 51 excites a nucleic acid sample to generate excited light and photographs images of the excited light ejected from the nucleic acid sample. The nucleic acid sequencing imaging method uses a super-resolution imaging method to excite a nucleic acid sample to eject excited light and to photograph images of the excited light. The super-resolution imaging method may be any super-resolution imaging method introduced in the above embodiments or a super-resolution imaging method obtained by improvement of any super-resolution imaging method described above.

Figure 10:
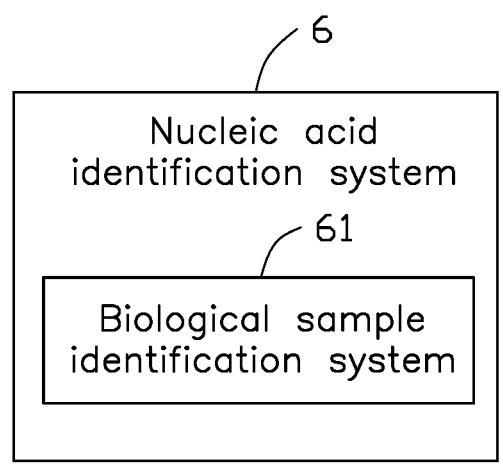
FIG. 10 is a schematic diagram of a nucleic acid identification system provided in an embodiment of the present disclosure.

The biological sample identification system and method described in the above embodiments can be used in nucleic acid sequencing. Specifically, the present application further provides a nucleic acid identification system and a nucleic acid identification method. Referring to FIG. 10, the nucleic acid identification system 6 includes a biological sample identification system 61. The biological sample identification system 61 may be any biological sample identification system introduced in the above embodiments or a biological sample identification system obtained by improvement of any biological sample identification system described above. The biological sample identification system 61 excites a nucleic acid sample to generate excited light and photographs images of the excited light ejected from the nucleic acid sample, and identifies a base class of the nucleic acid sample based on the images. The nucleic acid identification method uses a biological sample identification method to identify a base class of a nucleic acid sample. The biological sample identification method may be any biological sample identification method introduced in the above embodiments or a biological sample identification method obtained by improvement of any biological sample identification method described above.

In summary, using the super-resolution imaging system and method, the biological sample identification system and method, the nucleic acid sequencing imaging system and method, and the nucleic acid identification system and method provided in the embodiments of the present disclosure, a plurality of (e.g., 4) images of excited light are obtained by changing the direction and phase of an output illumination pattern of structured light, and image reconstruction is performed by using the plurality of images to obtain a super-resolution image, and the class and layout of the biological sample can be identified by using the super-resolution image; in application to nucleic acid sequencing, the base class and layout can be identified. As few excited light images need to be photographed, the speed of biological sample identification is improved; and in application to nucleic acid sequencing, the speed of base identification can be improved. Using the super-resolution imaging technology can improve the density of biological samples on the sample carrier, thereby solving the problems of low imaging efficiency, limited sample layout density, and low utilization of the sample carrier due to the use of ordinary wide-field fluorescence microscopy imaging technology in the prior art; and in application to nucleic acid sequencing, it can solve the problems of a low sequencing throughput, limited chip density, low chip utilization, and low utilization of reagents.

Finally, it should be noted that the above embodiments are only used for illustrating the technical solutions of the present disclosure rather than for limitations. Although the present disclosure is described in detail with reference to the preferred embodiments, those of ordinary skill in the art should understand that they can make modifications or equivalent substitutions to the technical solutions of the present disclosure without departing from the spirit and scope of the technical solutions of the present disclosure.

What is claimed is:

1. A super-resolution imaging system, comprising an illumination system and an imaging system, the illumination system being configured to output excitation light to irradiate a biological sample to generate excited light, and the imaging system being configured to collect and record the excited light to generate an excited light image, wherein the illumination system comprises an excitation light source and a structured light generation and modulation device, the excitation light source is configured to output the excitation light, the structured light generation and modulation device is configured to modulate the excitation light into structured light to irradiate the biological sample to generate the excited light, the structured light generation and modulation device comprises a polarization control system, a diffraction splitting device, and a structured light control device, the structured light control device being configured to control the structured light generation and modulation device to change a phase of the structured light output by the structured light generation and modulation device and a direction of an illumination pattern of the structured light projected on the biological sample, and the imaging system is configured to photograph images of excited light excited by excitation light of at least one wavelength in at least one imaging field of view, in conjunction with a change in the phase of the structured light and/or the direction of the illumination pattern;
   wherein the structured light control device is further configured to control the illumination pattern of the structured light to meet a preset contrast by controlling the polarization control system and the diffraction splitting device to move linearly together or rotate together.

2. The super-resolution imaging system according to claim 1, wherein the polarization control system is configured to adjust a polarization direction of the excitation light, the diffraction splitting device is configured to split the excitation light into multiple beams to form the structured light with a specific phase and a specific illumination pattern direction, and the structured light control device is configured to control the diffraction splitting device to change the phase of the structured light and the direction of the illumination pattern.

3. The super-resolution imaging system according to claim 2, wherein the structured light control device is configured to control the diffraction splitting device to move linearly to change the phase of the structured light, and to control the diffraction splitting device to rotate to change the direction of the illumination pattern of the structured light.

4. The super-resolution imaging system according to claim 3, wherein the super-resolution imaging system further comprises an objective lens, and the structured light generation and modulation device further comprises a focusing device, the focusing device is configured to focus the structured light ejected from the diffraction splitting device to the objective lens, and the objective lens is configured to eject the structured light as parallel light to the biological sample and form interference fringes at a certain angle on a plane of the biological sample.

5. The super-resolution imaging system according to claim 4, wherein the diffraction splitting device comprises a phase grating, and the polarization control system comprises a polarizer.

6. The super-resolution imaging system according to claim 5, wherein the phase grating and the polarizer together are arranged on a one-dimensional moving platform, and the one-dimensional moving platform is arranged on a turntable, and the structured light control device is configured to control the one-dimensional moving platform to bring the phase grating and the polarizer to into movement to change the phase of the structured light, and to control the turntable to bring the phase grating and the polarizer into rotation to change the direction of the illumination pattern of the structured light.

7. The super-resolution imaging system according to claim 5, wherein the focusing device comprises a first lens, a second lens and a third lens, with a stopper arranged between the first lens and the second lens, the stopper is configured to shield and block part of the structured light from entering a subsequent optical path.

8. The super-resolution imaging system according to claim 7, wherein the polarizer is configured to convert the excitation light into linearly polarized light, and the phase grating is configured to convert the linearly polarized light into +1st-order, −1st-order, and 0th-order diffracted light, the 0th-order diffracted light is blocked by the stopper, and the +1st-order diffracted light and the −1st-order diffracted light are focused to a back focal plane of the objective lens after passing through the second lens and the third lens.

9. The super-resolution imaging system according to claim 2, wherein the structured light generation and modulation device further comprises an adaptive optics device configured to shape a wavefront of the structured light.

10. The super-resolution imaging system according to claim 9, wherein the structured light control device is further configured to control the adaptive optical device to optimize a contrast and/or a uniformity of the structured light.

11. The super-resolution imaging system according to claim 1, being configured to irradiate a nucleic acid sample and photograph images of exited light ejected from the nucleic acid sample.

12. A super-resolution imaging method, comprising:
controlling an excitation light source of an illumination system in a super-resolution imaging system to be started, so that the illumination system outputs and irradiates structured light to a biological sample and the biological sample generates excited light;
controlling the structured light output from the illumination system to be in a first phase and an illumination pattern of the structured light to be in a first direction, and photographing a first image of the excited light;
controlling the structured light output from the illumination system to be in a second phase different from the first phase and the illumination pattern of the structured light to be in the first direction, and photographing a second image of the excited light;
controlling the structured light output from the illumination system to be in the second phase and the illumination pattern of the structured light to be in a second direction different from the first direction, and photographing a third image of the excited light; and/or
controlling the structured light output from the illumination system to be in the second phase and the illumination pattern of the structured light to be in a third direction different from the first direction and the second direction, or controlling the structured light output from the illumination system to be in the first phase and the illumination pattern of the structured light to be in the second direction, and photographing a fourth image of the excited light.

13. The super-resolution imaging method according to claim 12, wherein the structured light is controlled to be in different phases by linearly moving a diffraction splitting device of the illumination system, and the illumination pattern of the structured light is controlled to be in different directions by rotating the diffraction splitting device, and the illumination pattern of the structured light in each direction and each phase meets a preset requirement by controlling a polarization control system to move or rotate.

14. The super-resolution imaging method according to claim 12, wherein the illumination pattern of the structured light meeting a preset requirement comprises a contrast of the illumination pattern of the structured light meeting a preset requirement.

15. The super-resolution imaging method according to claim 12, further comprising: switching a wavelength of the excitation light and repeating steps of switching the phase and/or the direction of the structured light and photographing images of the excited light.

16. The super-resolution imaging method according to claim 12, after steps of switching the phase and/or the direction of the structured light and photographing an image of the excited light, further comprising: switching the wavelength of the excitation light and repeating the switching and photographing step.

17. The super-resolution imaging method according to claim 12, further comprising: switching an imaging field of view of the super-resolution imaging system and repeating steps of switching the phase and/or the direction of the structured light and photographing images of the excited light.

18. The super-resolution imaging method according to claim 12, after steps of switching the phase and/or the direction of the structured light and photographing an image of the excited light, further comprising: switching an imaging field of view of the super-resolution imaging system and repeating the switching and photographing step.

19. The super-resolution imaging method according to claim 12, being configured to excite a nucleic acid sample to eject excited light and to photograph images of the excited light.

* * * * *